(12) United States Patent
LeBlond et al.

(10) Patent No.: US 7,855,651 B2
(45) Date of Patent: Dec. 21, 2010

(54) SYSTEM FOR MONITORING AND RECORDING HAND HYGIENE PERFORMANCE

(75) Inventors: Claude W. LeBlond, Irvine, CA (US); Henry M. Ortiz, Aliso Viejo, CA (US)

(73) Assignee: Cognetive Systems Incorporated, Irvine, CA (US)

(*) Notice: Subject to any disclaimer, the term of this patent is extended or adjusted under 35 U.S.C. 154(b) by 0 days.

(21) Appl. No.: 12/634,408

(22) Filed: Dec. 9, 2009

(65) Prior Publication Data

US 2010/0153374 A1 Jun. 17, 2010

Related U.S. Application Data

(63) Continuation-in-part of application No. 11/784,429, filed on Apr. 6, 2007, now abandoned.

(60) Provisional application No. 60/790,380, filed on Apr. 7, 2006.

(51) Int. Cl.
*G08B 13/14* (2006.01)
(52) U.S. Cl. ............... 340/573.1; 222/23; 4/619
(58) Field of Classification Search .......... 340/539.1, 340/539.13, 573.1; 702/176; 222/23, 52; 4/619, 623
See application file for complete search history.

(56) References Cited

U.S. PATENT DOCUMENTS

| | | | |
|---|---|---|---|
| 3,478,344 A | 11/1969 | Schwitzgebel et al. |
| 3,764,984 A | 10/1973 | McCartney |
| 3,805,265 A | 4/1974 | Lester |
| 4,119,948 A | 10/1978 | Ward et al. |
| 4,254,472 A | 3/1981 | Juengel et al. |
| 4,375,637 A | 3/1983 | Desjardins |
| 4,538,138 A | 8/1985 | Harvey et al. |
| 4,567,557 A | 1/1986 | Burns |
| 4,743,892 A | 5/1988 | Zayle |
| 4,746,907 A | 5/1988 | Zehnder, Jr. |
| 4,896,144 A | 1/1990 | Bogstad |
| 5,202,666 A | 4/1993 | Knippscheer |
| 5,610,589 A | 3/1997 | Evans et al. |
| 5,611,465 A | 3/1997 | Lee et al. |
| 5,691,919 A | 11/1997 | Gemmell et al. |
| 5,745,049 A | 4/1998 | Akiyama et al. |
| 5,812,059 A | 9/1998 | Shaw et al. |
| 5,878,381 A | 3/1999 | Gemmell et al. |
| 5,900,801 A | 5/1999 | Heagle et al. |
| 5,905,436 A | 5/1999 | Dwight et al. |
| 5,910,776 A | 6/1999 | Black |
| 5,917,425 A | 6/1999 | Crimmins et al. |
| 5,939,974 A | 8/1999 | Heagle et al. |

(Continued)

*Primary Examiner*—Jeffery Hofsass
(74) *Attorney, Agent, or Firm*—Blakely Sokoloff Taylor & Zafman LLP

(57) ABSTRACT

A hand hygiene behavior management system capable of monitoring and recording information generated by the operation of dispensers as a method of assessing behavior of a group as an indication of overall hygiene performance. The system generally includes a plurality of wireless communication devices with a first number of the wireless communication devices being disposed within or adjacent dispensers and operatively configured for sensing, monitoring and reporting information about the status and operation of the dispensers. A hierarchal communication network for access to a central host database; a data processor and hygiene management application software operatively configured to create hygiene management reports based upon the monitored dispenser data and a method to provide user interface.

20 Claims, 13 Drawing Sheets

U.S. PATENT DOCUMENTS

| | | | |
|---|---|---|---|
| 5,945,910 A | 8/1999 | Gorra | |
| 5,952,924 A | 9/1999 | Evans et al. | |
| 5,959,533 A | 9/1999 | Layson, Jr. et al. | |
| 5,973,601 A | 10/1999 | Campana, Jr. | |
| 6,000,429 A | 12/1999 | Van Marcke | |
| 6,002,334 A | 12/1999 | Dvorak | |
| 6,037,871 A | 3/2000 | Babylon | |
| 6,038,331 A | 3/2000 | Johnson | |
| 6,053,197 A | 4/2000 | Gorges | |
| 6,072,396 A | 6/2000 | Gaukel | |
| 6,100,806 A | 8/2000 | Gaukel | |
| 6,124,806 A | 9/2000 | Cunningham et al. | |
| 6,195,006 B1 | 2/2001 | Bowers et al. | |
| 6,195,588 B1 | 2/2001 | Gauthier et al. | |
| 6,211,788 B1 | 4/2001 | Lynn et al. | |
| 6,225,906 B1 | 5/2001 | Shore | |
| 6,236,317 B1 | 5/2001 | Cohen et al. | |
| 6,236,953 B1 | 5/2001 | Segal | |
| 6,353,764 B1 | 3/2002 | Imagawa et al. | |
| 6,360,181 B1 | 3/2002 | Gemmell et al. | |
| 6,375,038 B1 | 4/2002 | Daansen et al. | |
| 6,392,546 B1 | 5/2002 | Smith | |
| 6,396,413 B2 | 5/2002 | Hines et al. | |
| 6,411,920 B1 | 6/2002 | McConnell et al. | |
| 6,425,411 B1 | 7/2002 | Gorges | |
| 6,426,701 B1 | 7/2002 | Levy et al. | |
| 6,532,416 B1 | 3/2003 | Mueller | |
| 6,549,816 B2 | 4/2003 | Gauthier et al. | |
| 6,701,194 B2 | 3/2004 | Gauthier et al. | |
| 6,727,818 B1 | 4/2004 | Wildman et al. | |
| 6,750,773 B2 | 6/2004 | Higgins | |
| 6,796,799 B1 | 9/2004 | Yoshiike et al. | |
| 6,882,278 B2 | 4/2005 | Winings et al. | |
| 6,895,296 B2 | 5/2005 | Holt et al. | |
| 6,898,552 B2 | 5/2005 | Marcichow | |
| 6,956,498 B1 | 10/2005 | Gauthier et al. | |
| 6,973,939 B2 | 12/2005 | Gorges et al. | |
| 6,975,231 B2 | 12/2005 | Lane et al. | |
| 7,099,649 B2 | 8/2006 | Patterson et al. | |
| 7,177,725 B2 | 2/2007 | Nortier et al. | |
| 7,242,307 B1 | 7/2007 | LeBlond et al. | |
| 2001/0025349 A1 | 9/2001 | Sharood et al. | |
| 2002/0135486 A1 | 9/2002 | Brohagen et al. | |
| 2002/0175182 A1 | 11/2002 | Matthews | |
| 2003/0030562 A1 | 2/2003 | Lane et al. | |
| 2003/0210140 A1 | 11/2003 | Menard et al. | |
| 2004/0012524 A1 | 1/2004 | Couronne et al. | |
| 2005/0035862 A1 | 2/2005 | Wildman et al. | |
| 2005/0134465 A1 | 6/2005 | Rice et al. | |
| 2005/0145745 A1 | 7/2005 | Lewis et al. | |
| 2005/0149414 A1 | 7/2005 | Schrodt et al. | |
| 2005/0171634 A1 | 8/2005 | York et al. | |
| 2005/0197732 A1 | 9/2005 | Holt et al. | |
| 2005/0248461 A1 | 11/2005 | Lane et al. | |
| 2006/0005312 A1 | 1/2006 | Reddy et al. | |

FIGURE 12

SYSTEM FOR MONITORING AND RECORDING HAND HYGIENE PERFORMANCE

CROSS-REFERENCE TO RELATED APPLICATIONS

This application is a continuation-in-part of U.S. patent application Ser. No. 11/784,429 filed Apr. 6, 2007, which claims the benefit of U.S. Provisional Patent Application No. 60/790,380 filed Apr. 7, 2006.

BACKGROUND OF THE INVENTION

1. Field of the Invention

The present invention relates to personal hygiene. More particularly, the present invention relates to a management system for remotely monitoring data generated by the function of a dispenser and transmitting the monitored information to a database where the implementation of software programs can create management information reports documenting hand hygiene performance.

2. Prior Art

U.S. Pat. No. 6,375,038 B1 to Daansen, teaches a soap dispenser that is a teaching tool and uses audio and visual means to promote compliance with proper washing techniques.

U.S. Pat. No. 5,945,910 to Gorra, teaches a monitoring module that operates in conjunction with an existing soap dispenser to track usage by individuals and provides a means of administrator review of the data.

U.S. Pat. No. 6,727,818 to Wildman, et al. describes a method of wirelessly monitoring hygiene compliance in a healthcare environment. The method comprises the steps of receiving location information of individuals and objects to determine movement and hand washing information to determine whether a person who has entered a patient contact zone has washed their hands since their most recent exposure to a contamination zone.

U.S. Pat. No. 5,900,801 to Heagle, et al. describes a system for monitoring and controlling a plurality of individual food establishment monitoring and controlling systems for a plurality of remotely located, separate food establishments. Each individual food establishment system includes a main computer with appropriate peripherals and an interface unit. The interface unit is also connected to a plurality of control devices which both monitor and control essential activities, including sanitation, temperature, signals for smoke detection, Ph levels, inventory and employee activities.

U.S. Pat. No. 6,426,701 to Levey, et al. teaches a system where a badge worn by the individual indicates a hand washing requirement through visual or audible means. The badge is location sensitive giving prompts based on signals received from a transmitting beacon. An individual must wash to clear the badge alarm. Handwash performance data for individual badge wearers are collected and stored in a database.

BRIEF DESCRIPTION OF THE DRAWINGS

FIG. 12 shows an administrative user interface screen which is functional for the administrative viewing of the activity of users accessing the User Interface Software Application.

DETAILED DESCRIPTION OF THE PREFERRED EMBODIMENTS

Figure 1:
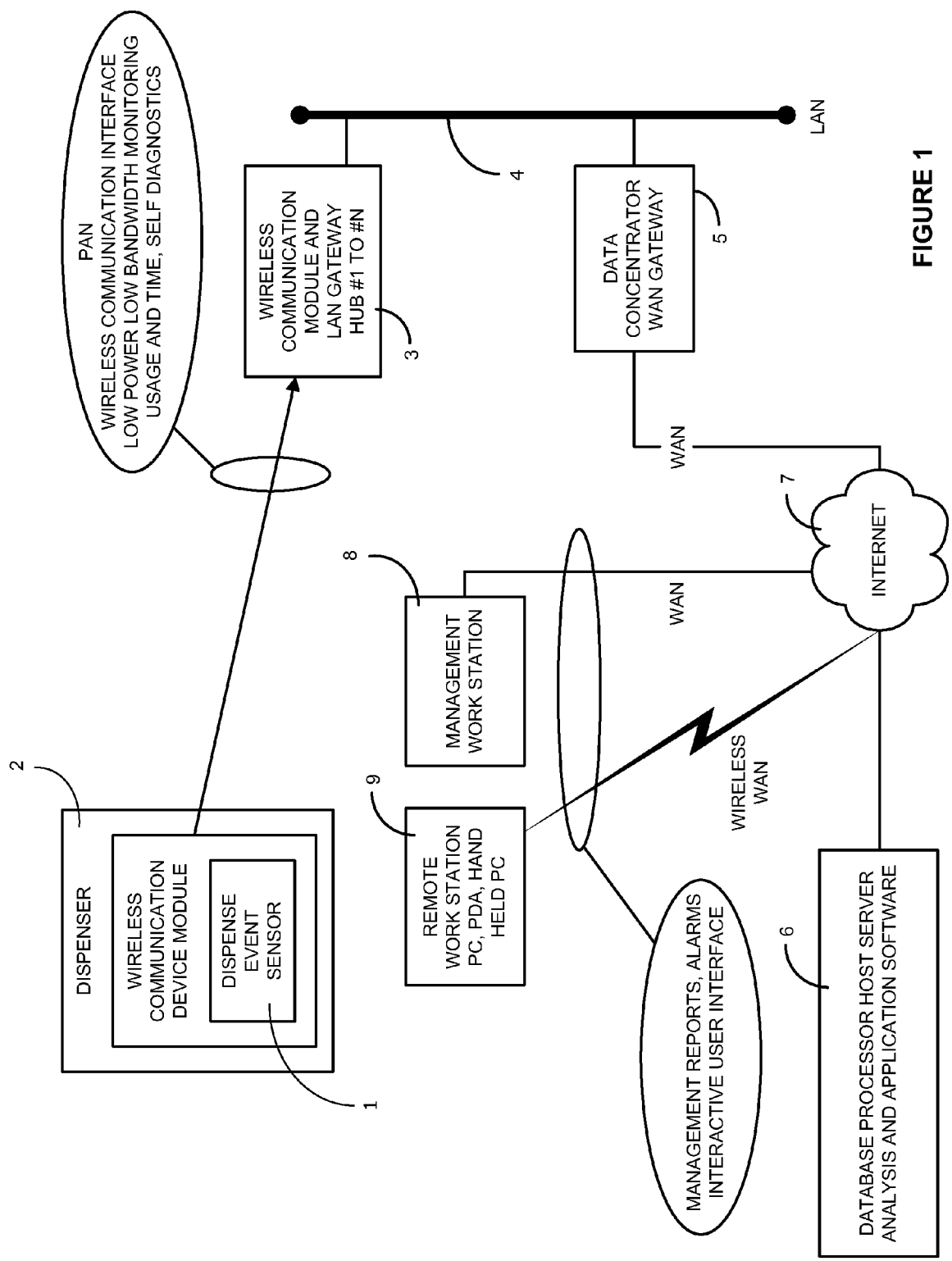
FIG. 1 is a block diagram of a hand hygiene monitoring system in accordance with the present invention showing one dispenser element.

The system described relates to a method for monitoring hygiene, and more particularly hand hygiene, such as in a food, health care, general office or industrial environment to determine the frequency and interval of hand washing practices. The system described is a remote monitoring system capable of monitoring and recording data generated by the function of a soap or sanitizer dispenser and in turn creating management information reports documenting hand hygiene practice behavior.

In recent years, the public's growing concern with disease and its transmission has generated increased public awareness of the topic of cleansing, and hygiene in general. Most major marketers in the cleansing and hygiene industry now believe that with increased public awareness and education, cleansing, and especially hand cleansing, will continue to be a subject of increasing scrutiny. As a result, industries such as the health care, food preparation, food services, and the hotel and travel industries have been forced to examine cleansing processes, procedures, and their efficacy.

Whether it is the possible transmission of *E. coli* in the food services industry, the rhinovirus in elementary schools, HAI diseases within health care facilities, or even the ordinary contact made during a simple handshake, there are numerous studies citing effective hand hygiene as the best way to guard against disease transmission. The CDC has concluded that hand washing is the single most important factor in the prevention of disease and the spread of infection. The need for, and effectiveness of proper hand hygiene is therefore well understood.

Non-compliance with established hand washing protocol is a serious problem with expensive and sometimes fatal consequences. Each year, food borne illness strikes 76 million people, causes 325,000 hospitalizations, and kills thousands. 70% of the outbreaks originate in the food service sector. 40% of these are the result of poor hand washing and cross contamination (oral/fecal).

The CDC estimates that Hospital Acquired Infections (HAI) infections cost on average $35,000 per incidence in extended medical costs. With respect to hospitals and hospital staff, it is estimated that the rate of hand washing non-compliance among health care workers is an astonishing 70-80%.

Recently verified by research at the University Of Pennsylvania School Of Medicine, the CDC also estimates that the occurrence of HAI can be reduced by one-third when infection control practices that include hand hygiene compliance measurement are implemented. The CDC estimates that the annual costs to the public health system, personal pain and suffering, and lost productivity that result from food-borne illness and HAIs are estimated to be as high as $83 billion annually. Approximately 2 million hospital patients annually become infected while being treated for another illness or injury. Of these 2 million infected patients, approximately 120,000 will die. The CDC estimates that these infections or illnesses add nearly $4.5 billion to U.S. health care costs annually. The CDC also estimates that one third of all HAI infections are caused by poor adherence to infection control practices, such as hand washing.

More specifically, in January 2004, Pennsylvania hospitals began submitting data on HAIs to the Pennsylvania Health Care Cost Containment Council (PHC4). While concerns remain about whether all hospitals are fully complying with this new initiative, the first year of data collected provides stunning information for all parties involved in the delivery and payment of hospital care. In 2004, Pennsylvania hospitals reported 11,668 HAIs, that is, 7.5 HAIs per 1,000 patients admitted to Pennsylvania's general acute care hospitals. 15.4% or 1,793 of these patients died. $2 billion in additional hospital charges and 205,000 additional hospital days were associated with the hospital admissions in which these devastating infections occurred.

In a study reported in the Journal of Infectious Diseases in Children, fecal coliforms were detected on the hands of some 20 percent of the daycare staff evaluated. Further, a third of the facilities studied had poor hand washing systems and no policy for hand washing before eating or after playing outside.

The Food and Drug Administration (FDA) assists the approximately 75 state and territorial agencies and more than 3,000 local departments that assume primary responsibility for preventing food borne illness, and for licensing and inspecting establishments within the retail segment of the food industry. This consists of more than one million establishments, and employs a work force of over 12 million. The FDA maintains a model Food Code to assist food control jurisdictions at all levels of government by providing them with a scientifically sound technical and legal basis for regulating the retail segment of the food industry. According to the model Food Code, a person must wash after using the bathroom, and defines a hand washing process with duration of a minimum 20 seconds with concentration on the fingers and fingernails. In addition to timing the process protocol of washing including the use of soap water is defined. Many operators in commercial food service have expanded on the FDA model with more rigorous protocols.

The monitoring of hand washing by individuals identified with badges and associating the badges and individuals with the use of hygiene dispensers is well known in prior art. The badge based hand wash monitoring systems have experienced only minor acceptance in the marketplace due to the complexities which result from the management of the badges as well as the effects of personal privacy concerns caused by the assignment of individual responsibility.

U.S. Pat. No. 6,375,038 B1 teaches a soap dispenser with a usage indicator which tracks the number of usages. The usage indicating or so called counting dispensers have experienced minor acceptance in the marketplace due to the burden of the manual recording and analysis of the count data from each dispenser.

It should be noted that a typical health care or food processing facility could have hundreds of dispensers and a similar number of individuals. It should also be noted that a typical food service facility could have only a few dispensers and the food service facility may be linked as a single unit to hundreds or thousands of similar facilities in a chain association.

An improvement on the manual process of data acquisition and analysis combined with the elimination of the individual responsibility of badge based identification in favor of group based hygiene behavior measurements in the context of the aforementioned environments where there are a many dispensers and many individuals in distributed locations is addressed in this disclosure.

A schematic representation of a system is shown in FIG. 1. Data are traced from event Sensor 1 in the dispenser 2 to the LAN Gateway Hub 3, through the LAN 4 to the Data Concentrator WAN Gateway 5 to the database processor host server 6 and showing output management report and alarms returning to the WAN 7 and then to fixed work stations 8 or portable communication devices 9, such as personal computers, or personal digital assistants communicated with a method to provide user interface.

Figure 2:
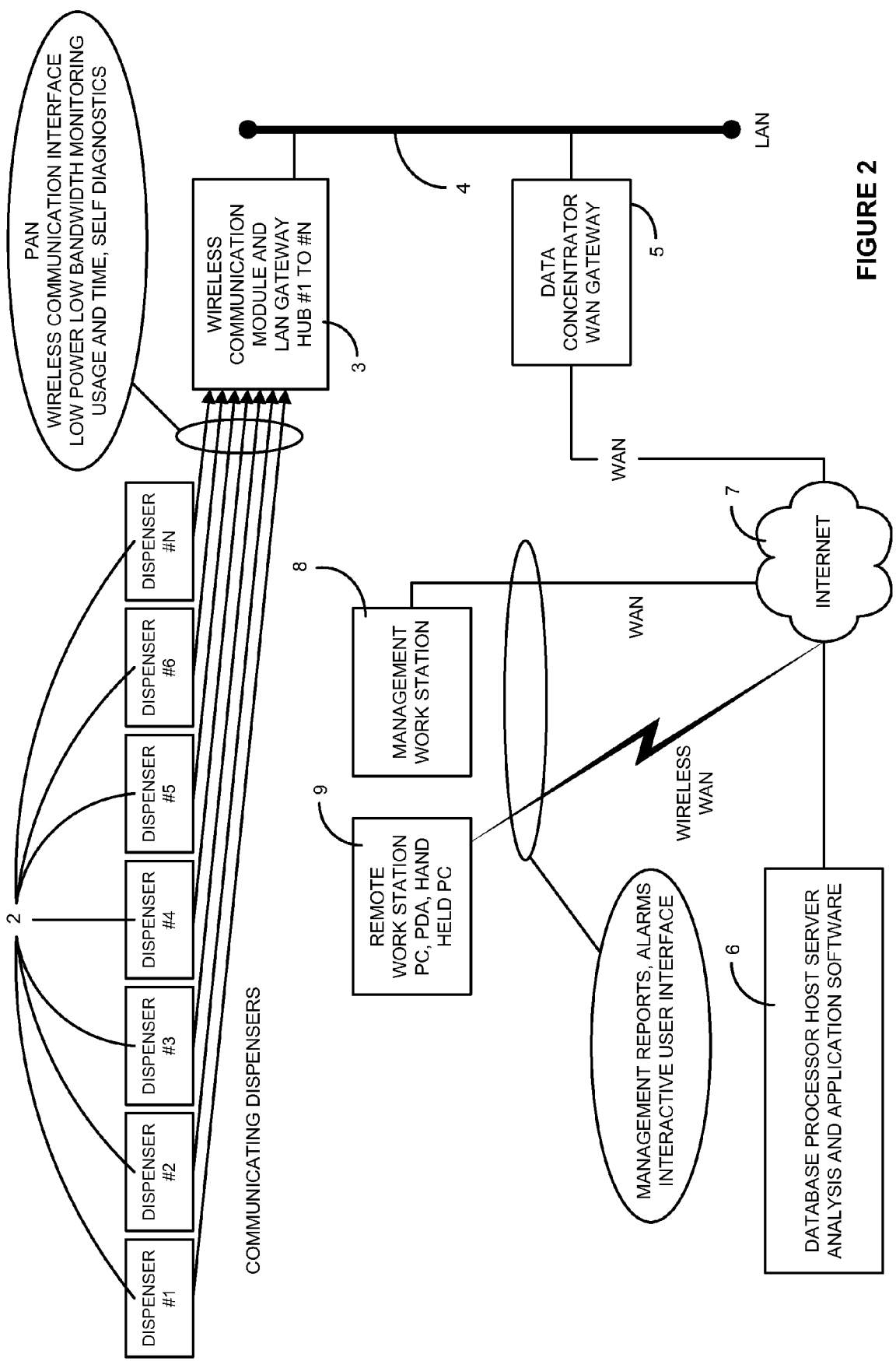
FIG. 2 is a block diagram of a hand hygiene monitoring system in accordance with the present invention showing multiple dispenser elements in multiple locations.

A schematic representation of a system with multiple dispensers 2 in multiple locations within a facility is shown in FIG. 2. and includes a data flow as previously described.

Figure 3:
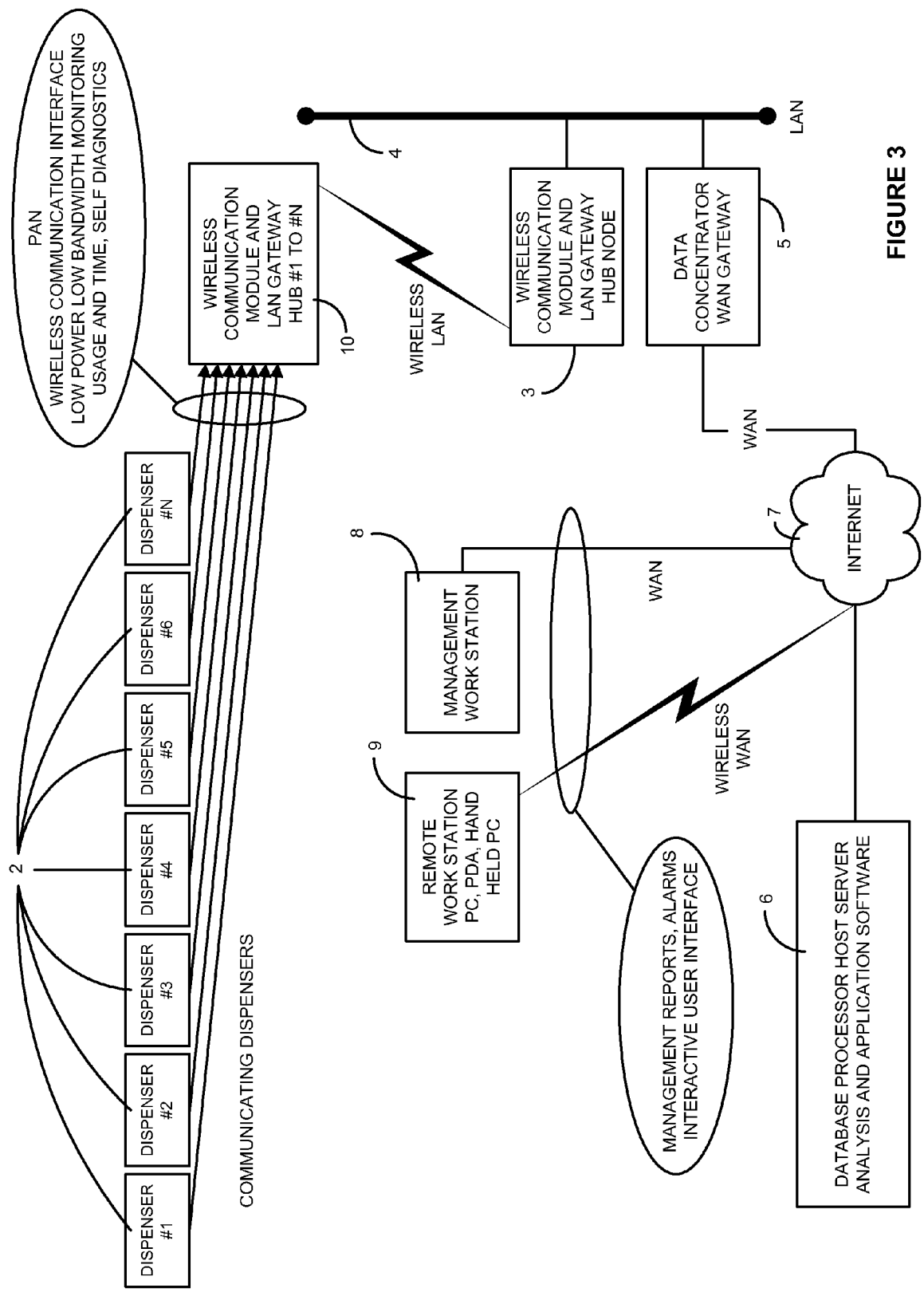
FIG. 3 is a block diagram of a hand hygiene monitoring system in accordance with the present invention showing multiple dispenser elements in multiple locations, including a wireless communication relay hub representing a number of 1 to n of possible relays.

A schematic representation of a system with multiple dispensers 2 in multiple locations within a facility including a wireless communication relay hub 10 representing a number of 1 to n of possible relays in the network serving to transmit data over long distance from the dispensers to the WAN gateway is shown in FIG. 3 and includes a data flow as previously described.

Figure 4:
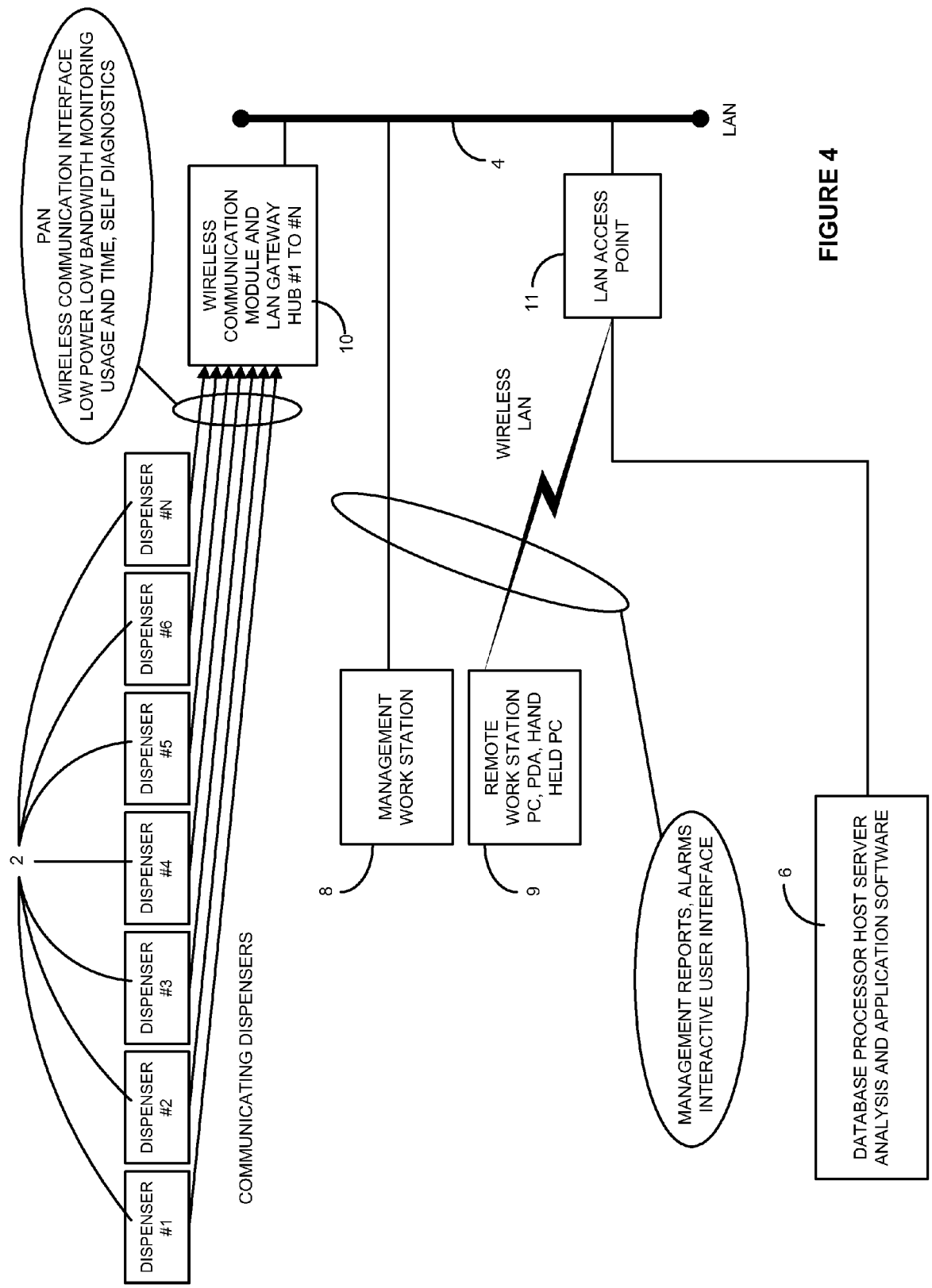
FIG. 4 is a variation of the hand hygiene monitoring system in accordance with the present invention where the database, data processor management application software, and user interface are contained locally in close proximity to the monitored dispenser elements.

The forgoing descriptions of the system for monitoring Wireless communication devices teach that there is communication to a Wide Area Network for access to a remote central host database, data processor and management application software and a method to provide user interface. A variation of the system is shown in FIG. 4 where the database, data processor management application software, and user interface are contained in close proximity to the monitored dispensers connected directly to the LAN or to the LAN wirelessly through a wireless access point 11.

A representation of a method of providing the user with an interface with the system for the purpose of determining hand wash behavior through the usage monitoring of individual dispensers is shown in FIGS. 5 through 13.

Figure 5:
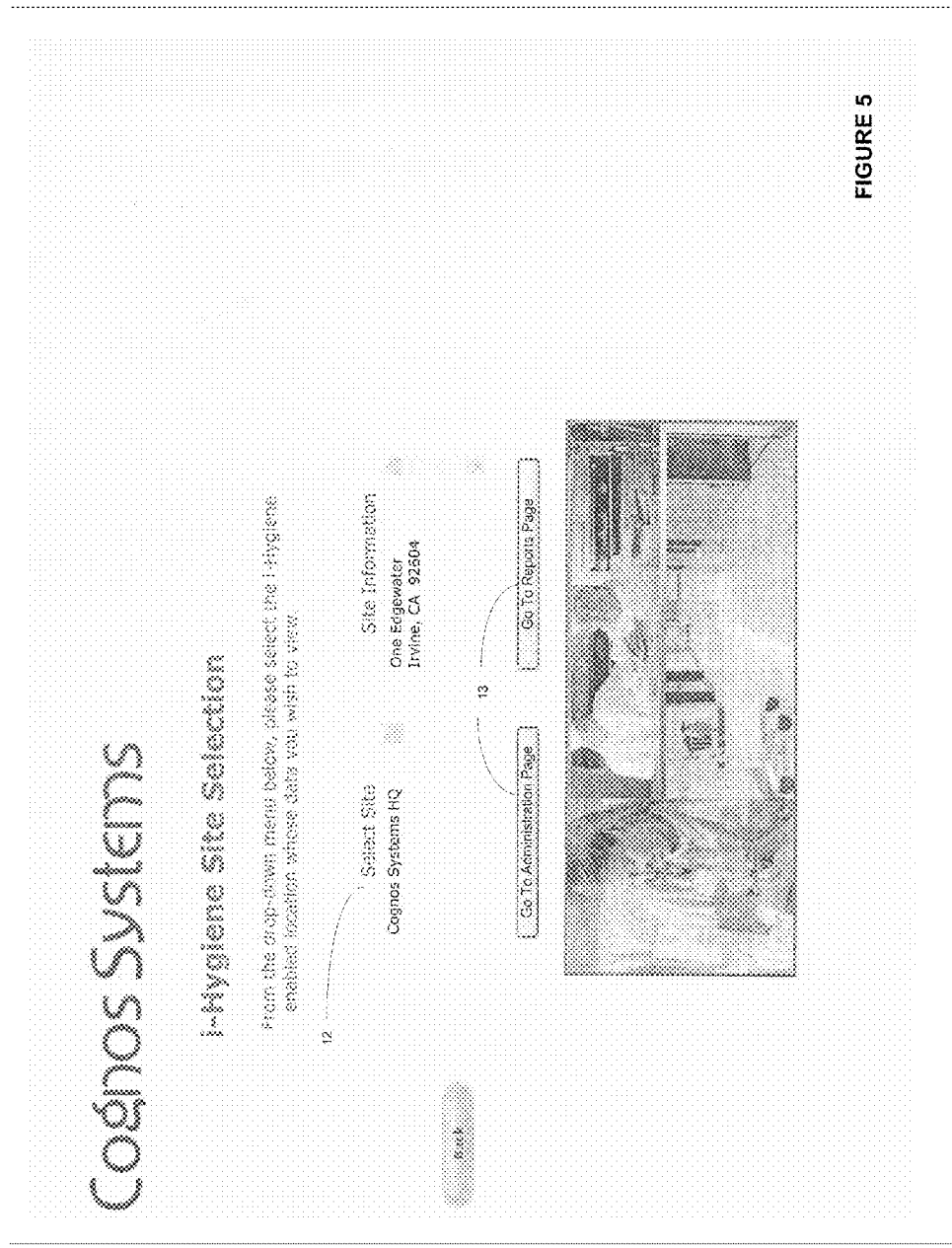
FIG. 5 shows a User Interface screen which provides functionality for the selection of the site where hand hygiene behavior data are to be viewed and for navigation to other screens.

FIG. 5 shows a User Interface screen which provides functionality for the selection of the site 12 where hand wash performance data are to be viewed and for navigation 13 to other screens.

Figure 6:
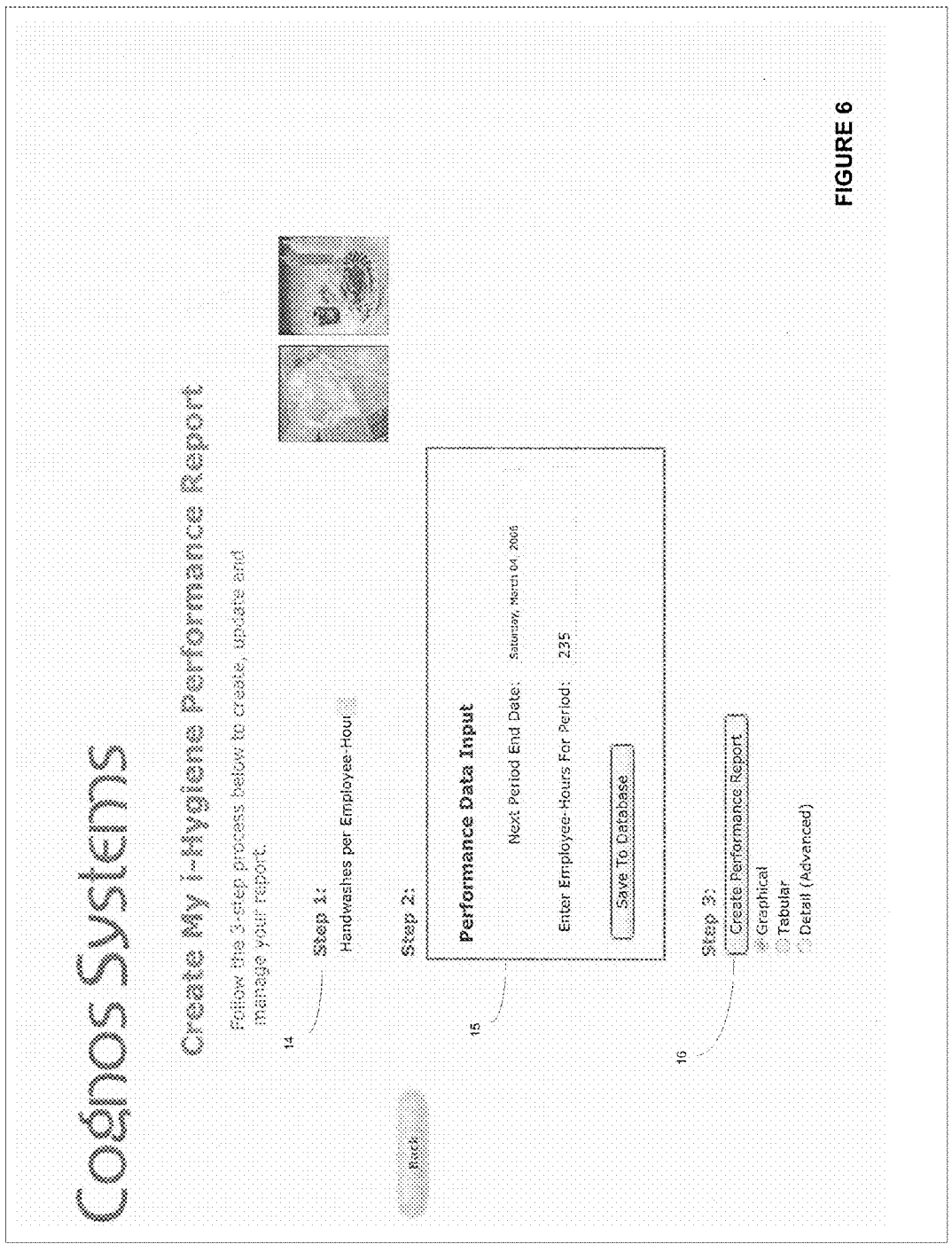
FIG. 6 shows a User Interface screen which provides functionality for the selection of a hand wash quotient metric and the type of report in which to display the hand hygiene behavior data.

FIG. 6 shows a User Interface screen which provides functionality for the selection of a hand wash quotient metric 14, the insertion into the database of the denominator value 15 of that quotient and the creation of hand wash performance data selectable in graphical or tabular formats 16. Step one in the process is to select the performance metric for available options examples of which are Handwashes per Employee Payroll Hour, Handwashes per Meal Served, Handwashes per patient visit and Hand washes per Patent Bed Day. Step two is to enter the numerical value of the metric quotient denominator selected in step one and save it to the database. The software application calculates the quotient of the Handwash events in the data base and the value entered. Step three is to select the type of report to display the handwash performance data from a selection of options including graphical and tabular.

In an alternative embodiment, the denominator value and metric definition can be entered automatically into the calculation through an interface with another database. For example, a financial business management software system may provide the metric quotient as payroll hours, patient days, meals cooked or customers served. A building management software system may provide the metric value in terms of lavatory door openings, or toilet flushes.

Figure 7:
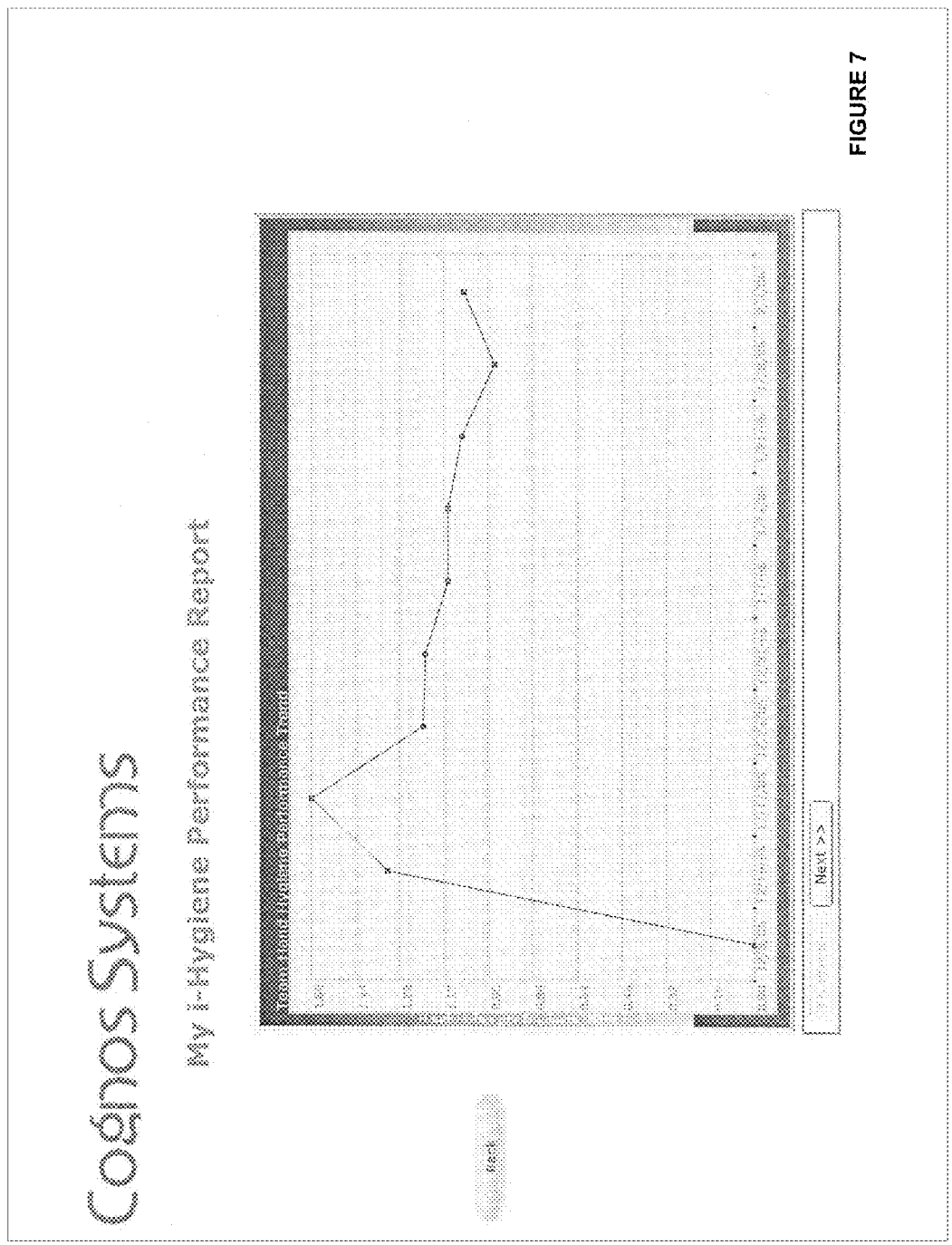
FIG. 7 shows a user interface screen which is a graphical display representation of the hand hygiene behavior.

FIG. 7 shows a user interface screen which is a graphical display representation of the number of dispense events or an associated number of hand washes monitored by the system over a defined period of time divided by the metric quotient denominator value entered in step two of the report Generation Screen described in FIG. 6 or through the alternative embodiment previously described. The Ordinate displays the quotient value calculated while the Abscissa displays the date the calculation is effective.

Figure 8:
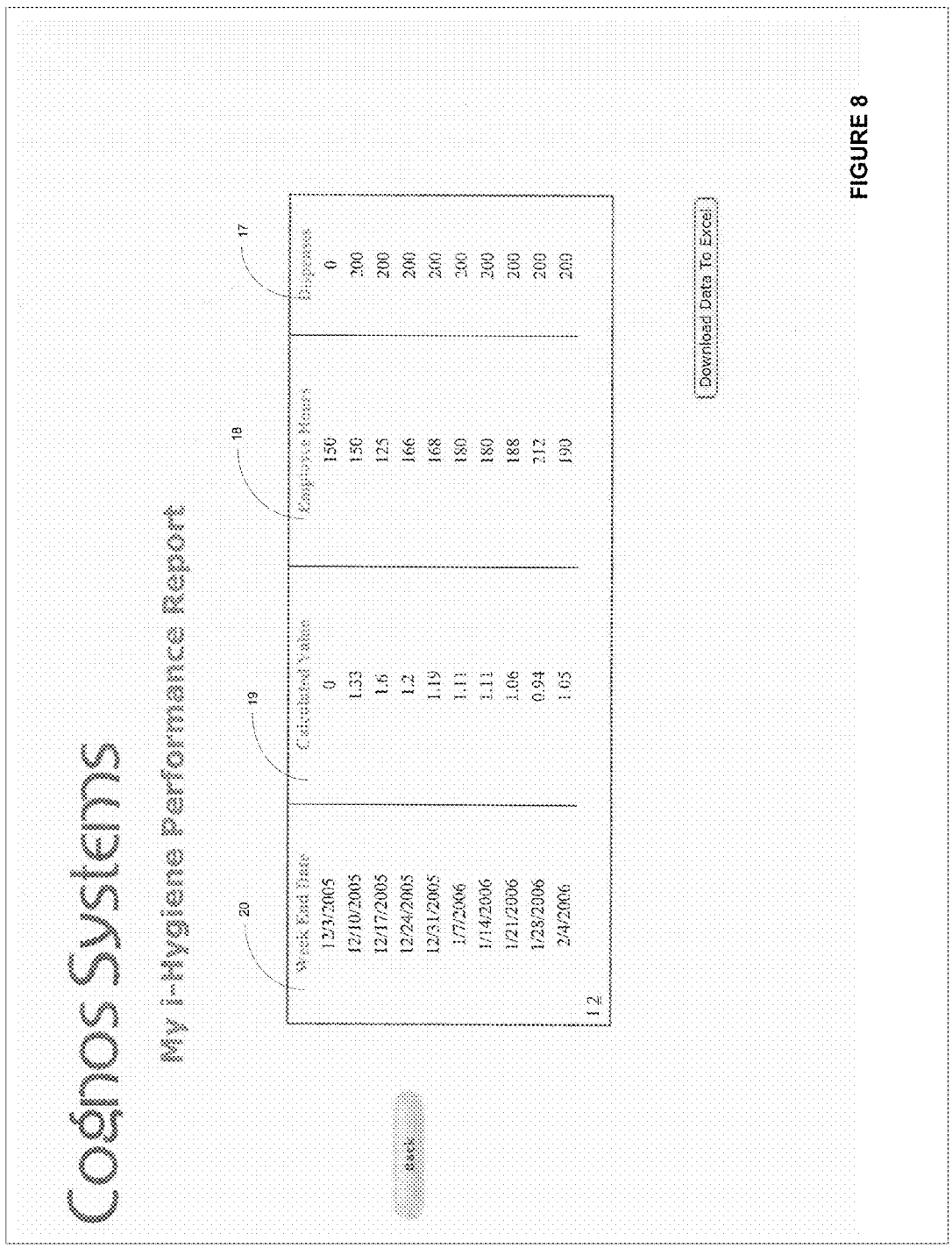
FIG. 8 shows a user interface screen which is a tabular display representation report created as described in FIG. 6.

FIG. 8 shows a user interface screen which is a tabular display representation report created as described in FIG. 6 previously and includes a display of the dispense events or associated Handwashes monitored by the system 17, the value of the metric quotient denominator 18 entered in step two as described in FIG. 6 or through the alternative embodiment previously described, the value of the quotient calculated 19 and the date at which the quotient is effective 20.

Figure 9:
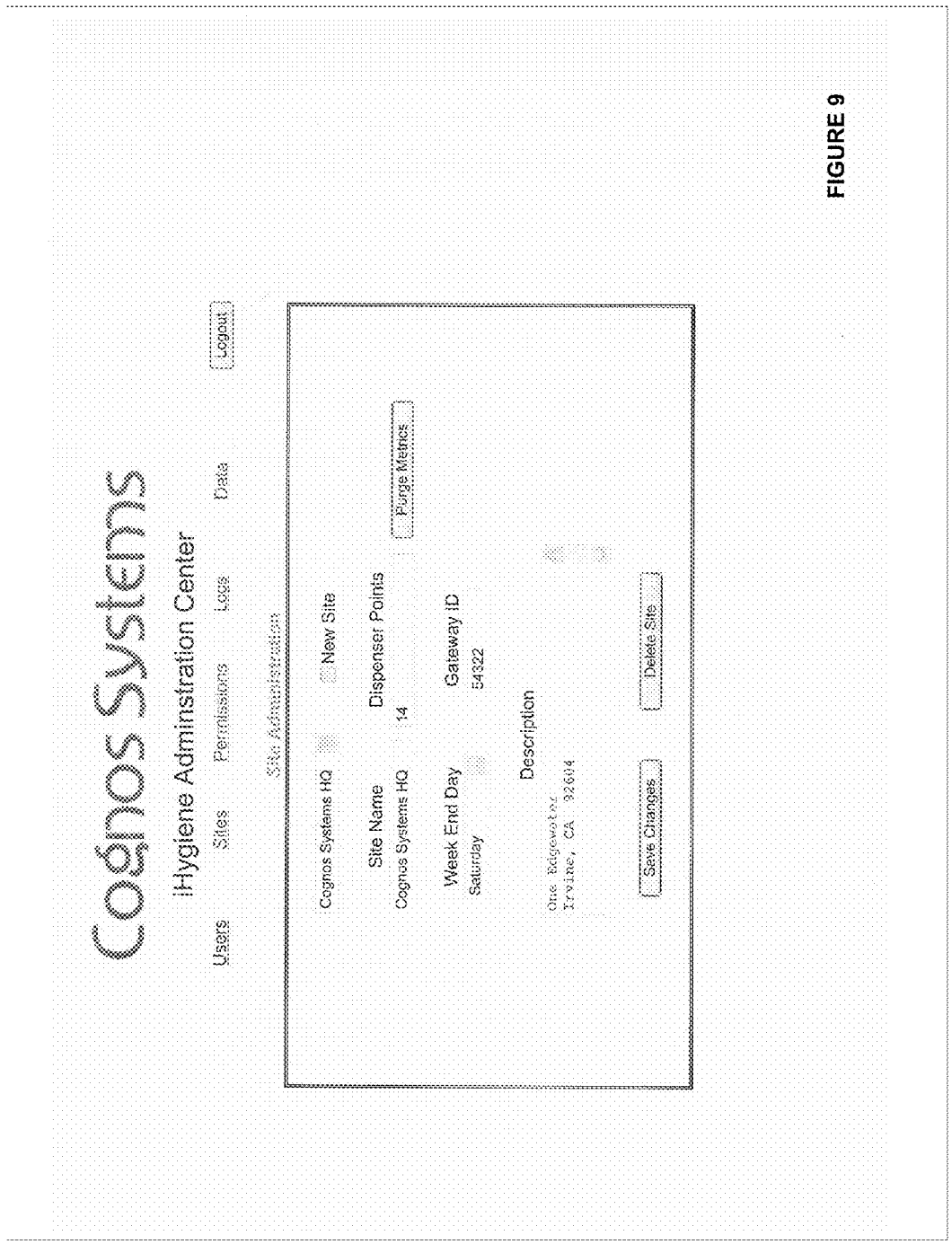
FIG. 9 shows an administrative user interface screen which is functional for the administration of variables associated with locations where handwash events are monitored. These locations are defined as Sites.

FIG. 9 shows an administrative user interface screen which is functional for the administration of variables associated with locations where handwash events are monitored. These locations are defined as Sites.

Figure 10:
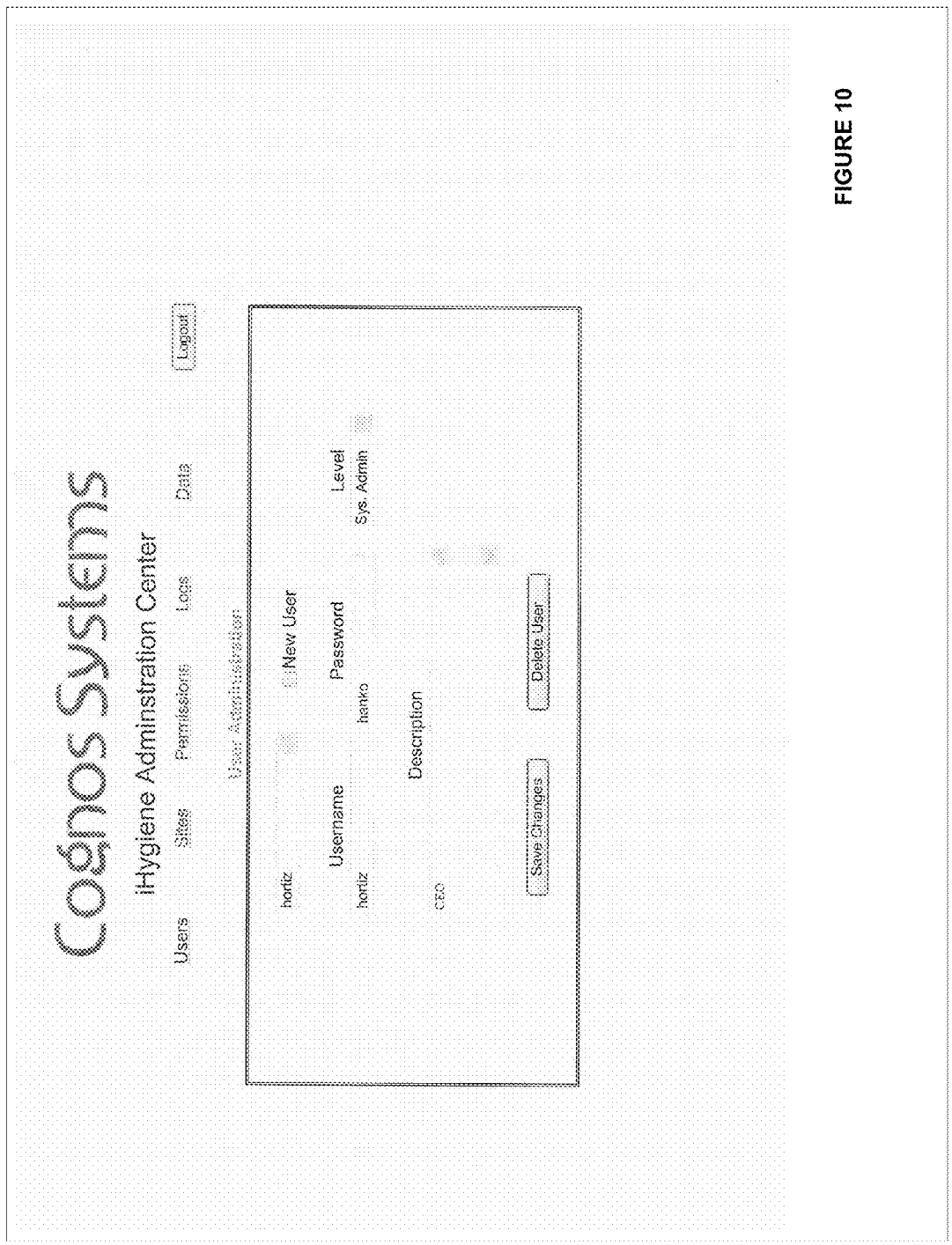
FIG. 10 shows an administrative user interface screen which is functional for the administration of variables associated with users and administrators of the User Interface Software Application.

FIG. 10 shows an administrative user interface screen which is functional for the administration of variables associated with users and administrators of the User Interface Software Application.

Figure 11:
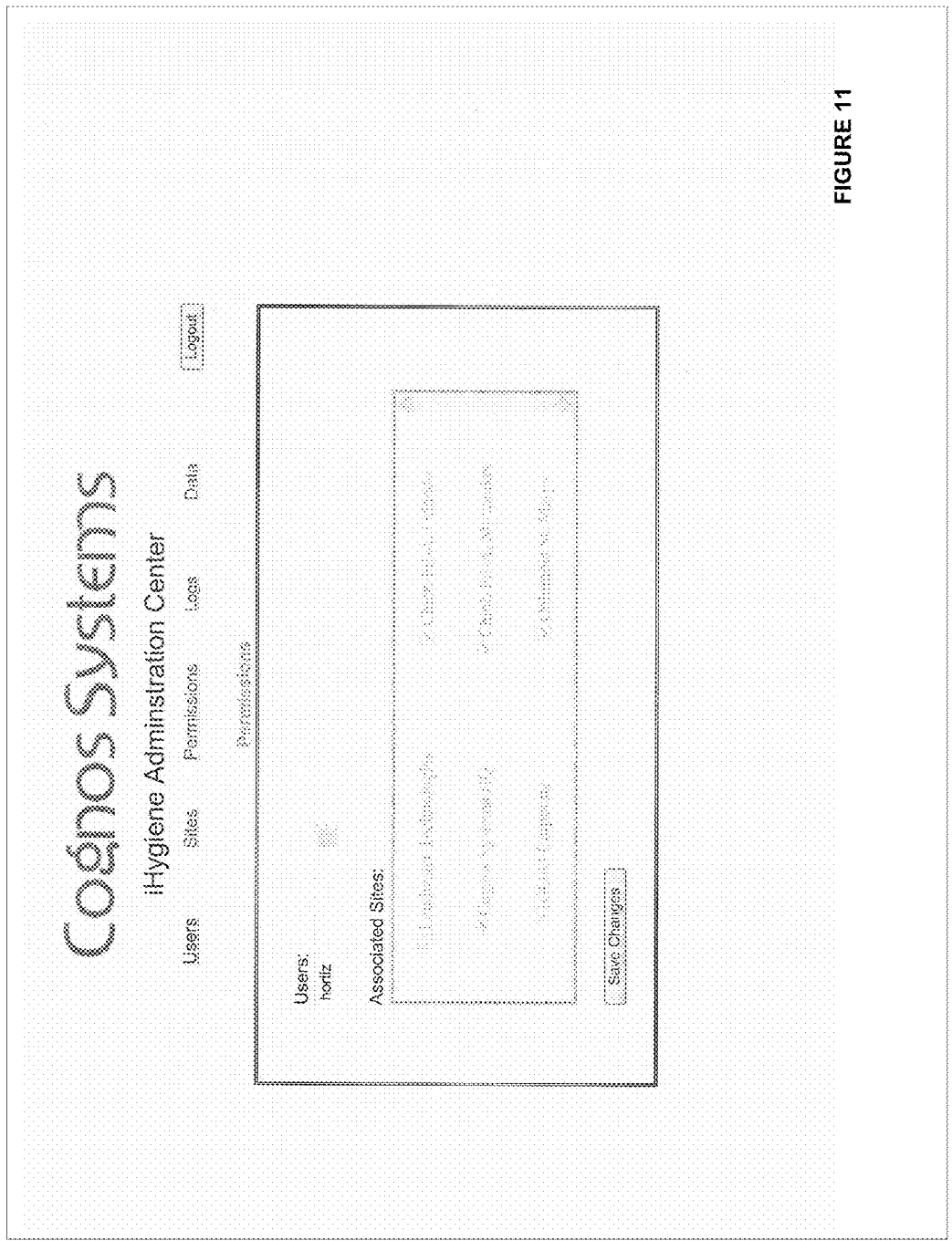
FIG. 11 shows an administrative user interface screen which is functional for the administration of variables associated with the access to Site data by Users of the User Interface Software Application.

FIG. 11 shows an administrative user interface screen which is functional for the administration of variables associated with the access to Site data by Users of the User Interface Software Application.

Figure 12:
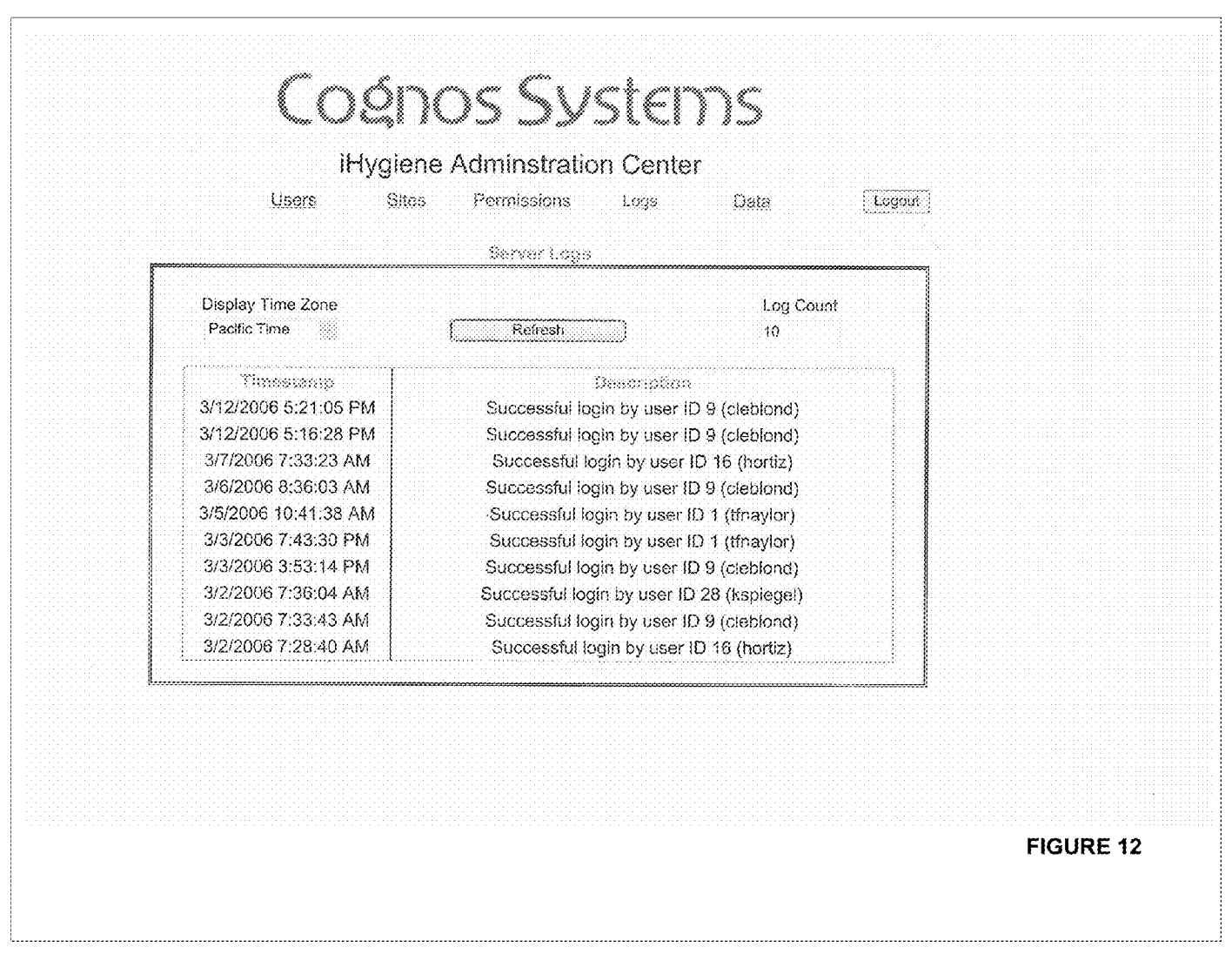

FIG. 12 shows an administrative user interface screen which is functional for the administrative viewing of the activity of users accessing the User Interface Software Application.

Figure 13:
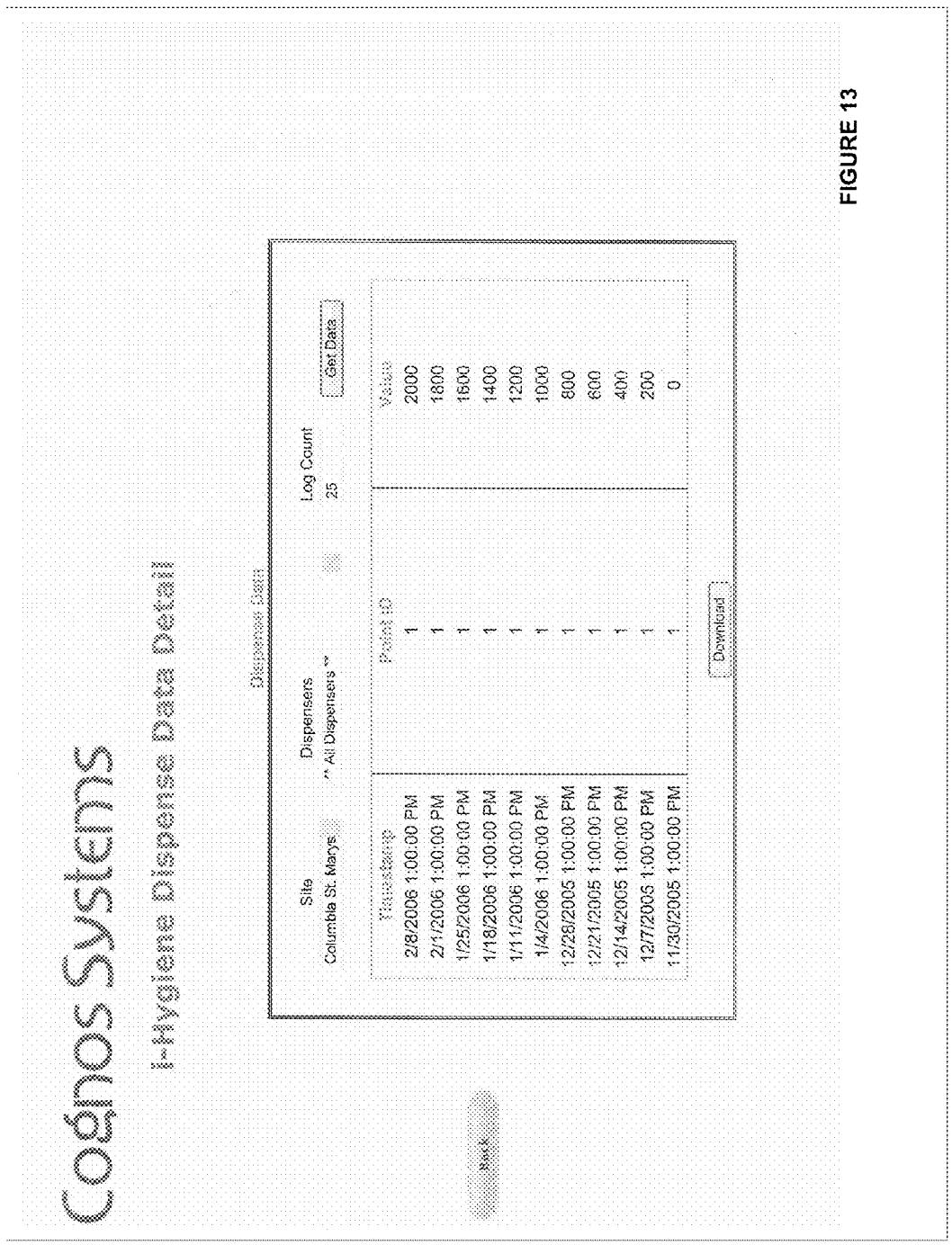
FIG. 13 shows an administrative user interface screen which is functional for the administrative viewing of the handwash events of dispenser elements monitored by the system.
Figure 7:
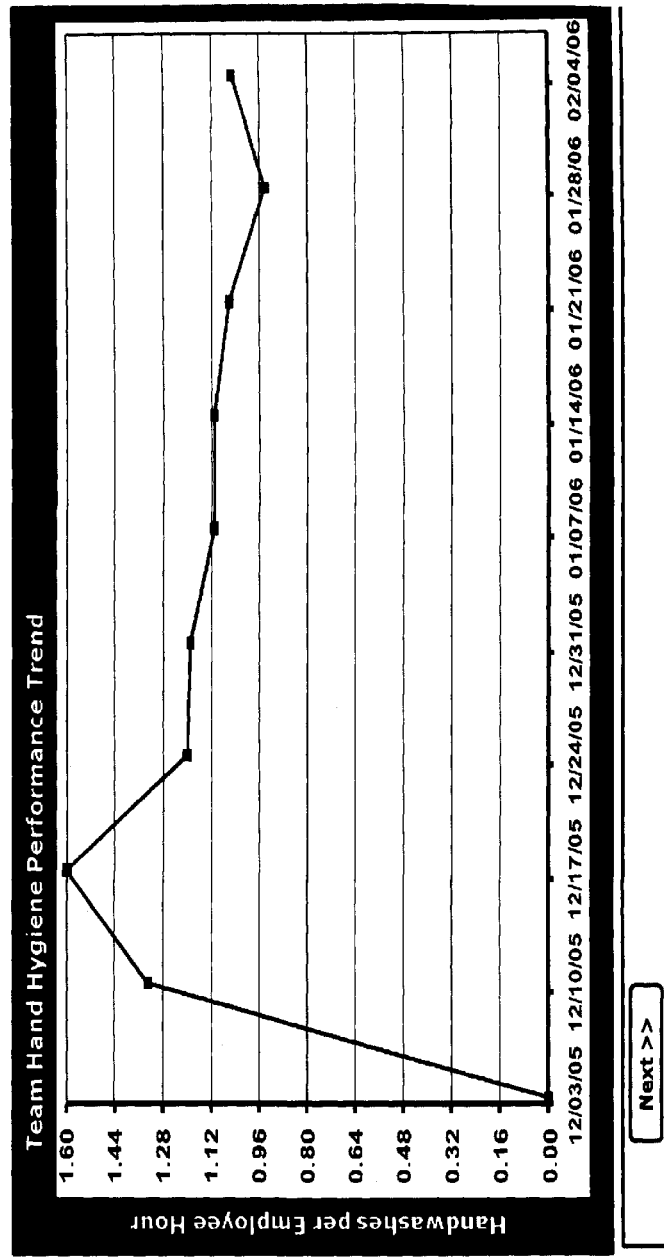

FIG. 13 shows an administrative user interface screen which is functional for the administrative viewing of the handwash events of dispensers monitored by the system.

The system described herein is a fully integrated wireless data collection, hierarchical network communication, telemetry, data base storage and analysis system which combines wireless Radio Frequency communication technology, dispenser operation sensors, network communication infrastructure, database and analysis software, management and reporting software and a method of providing management with an interface with the system for the purpose of determining hand wash behavior through the usage monitoring of individual dispensers.

The system is composed of a plurality of dispensers; each dispenser has an associated wireless communication device fixed in close proximity or integral to the dispenser such that the detection of a dispenser event is ascribed uniquely to the dispenser. The associated wireless communication device is a low power, low bandwidth radio frequency wireless communication device. Low power low bandwidth communication contributes to long battery life. The wireless communication device has the capability to broadcast information derived from the monitored dispenser event as well as the time and a unique code identifier of the dispenser.

The multiplicity of low power low bandwidth wireless RF communication devices create a Personal Area Network (PAN) and communicate with a higher power, higher bandwidth, wireless communication device and Local Area Network (LAN) Gateway Hub which collects, sorts and relays the data gathered from all the dispensers in its reception range to a facility LAN formed by a plurality of interconnected LAN Gateway Hubs which in turn communicate the dispenser data to a data concentrator and Wide Area Network (WAN) gateway. The data concentrator stores the data for periodic communication through the WAN gateway to the WAN as a conduit, and connects with a database data processor host data server which functions as a data storage device and a software application server which analyzes the status and use of the dispenser, generates management reports and alarms and is accessible through a local or remote portable management access device such as a PDA, hand held computer or fixed computer workstation.

It should be appreciated that a typical facility could have hundreds of dispensers forming a Personal Area Network with multiple LAN Gateway Hubs. The Gateway hubs forming a Local Area Network of Hubs which collect and aggregate the transmitted dispenser data and further communicate the dispenser data through the LAN to a single Data Concentrator WAN Gateway. By example, a typical health care facility may have multiple floors with hand wash stations on each floor. Each hand wash station may have multiple dispensers where data from many said dispensers may be collected by a fewer number of LAN Gateway Hubs on each floor. Each Hub is in communication with the other Hubs forming the LAN, collecting data from dispensers in their listening range on each floor and passing the aggregated data through the LAN from floor to floor until the data reach a single Data Concentrator WAN Gateway.

Thus, the network system is distributed and hierarchical with many dispensers in distributed locations transmitting data hierarchically to a smaller number of Gateway Hubs which in turn communicate collectively with a single Data Concentrator and WAN Gateway.

The wireless communication devices are short range (30 to 300 feet), radio frequency (RF) radio devices designed for point to point communication. The communication from point to point can be referred to as a personal Area Network (PAN). This communication can be one way communication or two way. One way communication reduces the complexity of network communication management and reduces the cost of individual devices. These devices can but do not need to operate in the unlicensed Industrial, Scientific & Medical (ISM) frequency bands. Battery power or harvested energy is the preferred method of supplying energy to these devices. These devices are designed to consume little power, drawing less than 10 mA when transmitting, and therefore promote long battery life. Because the data creation rate (bandwidth) of the dispensers being monitored is low, the transmission rate of the transmitter is low, typically below 1 kbps. A low transmission rate consumes less power and enables a less sophisticated and less expensive microprocessor. The volume of data are also low which requires a small communication transmission duration and consumes less power for each transmission. The RF devices suitable for use in the present invention include but are not limited to those available from many sources. Atmel Corporation, San Jose, Calif., LINX Technologies, Grants Pass, Oreg., Cypress Semiconductor, San Jose, Calif., RF Monolithics, Dallas Tex., Chipcon, Oslo, Norway. While the technology rapidly advances, Radiotronix, Moore, Okla. currently offers the preferred device in their model number RCT-433-AS.

Wireless communication devices and LAN Gateway Hubs suitable for use in the present invention are generally sophisticated RF transceiver devices with internal microprocessors. This sophisticated device is used as a single collecting node or as a relay in a larger hierarchal network of many similar devices. These devices communicate in a way determined by a communication protocol stored in the microprocessor. The protocol can be a proprietary design as demonstrated by the Zensys product or follow an industry standard assuring interoperability as demonstrated by IEEE Standard 802.15.4 known as ZigBee or IEEE standard 802.11 known as WiFi or IEEE standard 801.16 known as WiMax. This network typically extends the range and reliability of the sensing system by transferring the data from node to node in the LAN to the final device, a Data Concentrator and gateway connected to the WAN. These node devices are more expensive than the RF transmitter discussed previously due to their complexity. They consume more power, drawing as much as 36 mA when transmitting and require larger batteries or mains power. They are designed to carry a higher data Bandwidth of as much as 250 kbps. The devices are available from many sources including Crossbow Technology, San Jose, Calif., Dust, Berkeley, Calif., Ember, Boston, Mass., ZMD GMBH, Dresden, Germany and Linksys, Irvine, Calif.

The WAN gateway data concentrator is a communication device which stores data generated by the sensors and the data communicated to it by through the PAN to LAN network. The WAN gateway may contain a computing engine which processes these data to reconcile conflicting data, synthesize and format data into a communication protocol to be communicated through the WAN to the data processor host server. The WAN gateway may be programmed for outbound communication in the form of periodically scheduled general data transfers as well as asynchronous transfers in the event of special case alarms. The WAN gateway may be capable of bidirectional communication with the data processor/server through the WAN for the purpose of confirming that data transfers are completed with integrity or to facilitate reprogramming of the gateway from the data processor host server. Typically the WAN gateway serves a single facility and typically requires mains power.

It should be appreciated that the Personal Area Network (PAN) is a generic term referring to many possible forms, implementation schemes and hybrids describing a method of connectivity to a Local Area Network (LAN). While the preferred embodiment of the PAN is unidirectional, low power, low bandwidth, in the unlicensed frequency bands for the purpose of the extension of battery life, connectivity can be achieved a other radio frequencies, higher power and higher bandwidth. Bidirectional connectivity would allow feedback or control commands to be communicated to the monitored dispenser.

It should be appreciated that the facility Local Area Network (LAN) is a generic term referring to many possible forms, implementation schemes and hybrids describing a method of connectivity to a wide area network (WAN). Several typical examples of connection media are, Twisted Wire Pair Cable, Fiber Optic Cable, Coaxial Cable, Wireless Radio Frequency and Power Line transmission.

It should be appreciated that the Wide Area Network (WAN) is a generic term referring to many possible forms, implementation schemes and hybrids describing a method of connectivity to a remote database host server computing center. Examples of a Wide Area Network include the Internet, the wired telephone system and the wireless cell phone system.

The forgoing descriptions of the system for monitoring Wireless communication devices teach that there is hierarchal network communication to a Wide Area Network for access to a remote central host database, data processor and management application software and a method to provide user interface. It should be appreciated that the invention may be advantageously practiced using various sub-combinations of the embodiments disclosed. A variation of the system is taught where the database, data processor maintenance management application software, and user interface are contained locally in a work station communicating to the LAN in close proximity to the monitored dispensers.

It should also be appreciated that another variation of the disclosed embodiment of PAN to LAN to WAN hierarchal network communication progression of the monitored data may be avoided in an alternate embodiment where the dispenser communicates directly to the WAN without first passing data through a LAN or WAN gateway. Examples of this embodiment capability would include WAN communication technology incorporated in the dispenser. Examples are the aforementioned cellular telephone or WiMax communications devices.

Research from within several industries in which compliance with hand hygiene protocol is a requirement, and where hand hygiene performance or hand hygiene compliance rates are measured as a means of management or process control has shown that disease, death, stresses upon the health care system, and enormous avoidable expense may result due to non-compliance with minimum acceptable hand hygiene compliance rates.

Despite the fact that such a wealth of knowledge and understanding exists about the important benefits of compliance with hand hygiene protocols; and also the fact that prior art, technologies, and products exist which teach and provide methods for surveillance and acquisition of discrete hygiene event data, it is evident that the measurement of hand hygiene compliance rate as well as sustainable improvements in hand hygiene performance or compliance rates continue to be elusive. As a result, there is a significant amount of recent and ongoing research which examines various efforts to achieve not only a reliable method for measuring hand hygiene performance rates, but also achieving a measurable, and a sustainable improvement in hand hygiene compliance rates.

A hand hygiene event is typically described as the washing of one's hands with soap and water, or the rubbing of one's hands with an ethyl alcohol based hand rub or sanitizer. Both of the aforementioned hand hygiene events require the use of mechanical or electro-mechanical dispensing units which contain either liquid soap or an ethyl alcohol based gel. When an employee or co-worker executes a hand hygiene event, the hand hygiene event necessarily requires that either soap or alcohol gel be dispensed out of the dispenser, and into the employee or co-worker's hands so that a hand hygiene event may be performed. Hand hygiene events may be electronically sensed, counted and stored such as depicted in FIGS. 1-4.

Current research, as well as the World Health Organization (WHO) suggest that when seeking to establish or measure hand hygiene performance, it is not only the simple acquisition of discrete hygiene event data, or number or frequency of hand hygiene events that has occurred which must be measured, but more importantly, it is the number of hand hygiene events that have occurred taken together with and per the number of hand hygiene opportunities that has occurred. This more comprehensive set of information is required to yield a hand hygiene rate quotient, or hand hygiene compliance rate. This notion is supported by the WHO's Guidelines on Hand Hygiene in Health Care which suggests that the hand hygiene quotient or hand hygiene compliance rate should be calculated using the equation:

Hand Hygiene Rate=(Quantity of Hand Hygiene Events)/(Quantity of Hand Hygiene Opportunities)*100.

From the equation above it follows then that if an employee or co-worker has performed hand hygiene or executed a hand hygiene event just once, when in fact there were two distinct hand hygiene opportunities experienced by the employee or co-worker when hand hygiene should have been performed, the employee or co-worker's hand hygiene compliance rate could be computed using the equation above and said to be equal to 50%.

It is thus evident that, given a known quantity of hand hygiene events that has occurred during a given period of time, a denominator value which is equal to the number of hand hygiene opportunities that has also occurred during the same period of time is also required in order to obtain a hand hygiene quotient or hand hygiene compliance rate.

The WHO's Guidelines on Hand Hygiene in Health Care reinforce the importance of considering the quantity of hand hygiene events in addition to the number of hand hygiene opportunities experienced by health care workers when measuring, establishing, and evaluating hand hygiene performance and hand hygiene compliance rate. To support this position, the WHO's Guidelines on Hand Hygiene in Health Care set out to define the five hand hygiene moments, or hand hygiene opportunities, either before or after which a health care worker should perform hand hygiene. The WHO defines these five moments or opportunities as: Moment 1) Before Touching a Patient; Moment 2) Before a Clean/Aseptic Procedure; Moment 3) After Body Fluid Exposure Risk; Moment 4) After Touching a Patient; and Moment 5) After Touching Patient Surroundings.

While there are many ways to determine the number of hand hygiene events which transpire over time, within the health care community and within health care facilities, the quantity of hand hygiene opportunities, such as defined above and which has occurred over a specific period of time is typically established via human observation. The utilization of human observation in determining a hand hygiene opportunity quantity requires that specific staff or co-workers be trained in acutely recognizing when a hand hygiene opportunity has occurred, as well as how to observe co-workers unobtrusively, or even covertly such that an accurate assessment of the number of hand hygiene opportunities which has occurred during an observation session may be obtained. These trained observers are then responsible for occasionally observing the activities of co-workers in their day to day activities and counting the number of hand hygiene opportunities which occur during an occasional observation session. Thus, a hand hygiene compliance rate may be obtained via human observation by taking the ratio of hand hygiene events, however determined, to observed hand hygiene opportunities. The WHO's Hand Hygiene Technical Reference Manual suggests that approximately 200 observed hand hygiene opportunities per observation session are required to obtain hand hygiene compliance rates which may be reliably compared.

Thus the WHO's Guidelines on Hand Hygiene in Health Care specify a methodology for determining hand hygiene compliance rate, an equation to be used for computing hand hygiene compliance rate which utilizes the quantity of hand hygiene events in the equation numerator and hand hygiene opportunities in the equation denominator, and also provides a definition for hand hygiene opportunities. Furthermore, the WHO's Hand Hygiene Technical Reference Manual establishes how human observation should be performed in order to observe and count hand hygiene opportunities that have occurred during an observation session in order to establish a hand hygiene opportunity value or hand hygiene compliance equation denominator value.

It follows then, that the WHO's methodology and equation for determining hand hygiene compliance rate may be applied to areas outside of health care where hand hygiene compliance is not only a requirement, but also where a minimum hand hygiene compliance rate has been established, the number of discrete hand hygiene events performed by co-workers may be observed or electronically acquired, and also where a definition of hand hygiene opportunities may be established so that a hand hygiene rate denominator value may be determined.

It should be noted that within a hospital or similar health care facility, or even within a restaurant or food processing facility, there may be many different work areas which, by their very nature, pose varying types of hand hygiene opportunities which would be said to be typical of said work areas. Furthermore, different work areas within the same facility may demonstrate wide ranges in the typical quantity and frequency of hand hygiene opportunities.

As an example, within hospitals or similar health care facilities there are defined areas or wards that address the special and specific needs typical of various groups of the infirm. It is well known, for example, that within hospitals, the typical number of hand hygiene opportunities will vary dramatically by hospital ward type. Research literature points out that it is not uncommon to have a typical average of only eight hand hygiene opportunities per patient-hour in a pediatric ward, whereas the typical or average number of hand hygiene opportunities per patient-hour may be as high or higher than twenty in an intensive care ward. It can therefore be seen in the previous example, that an identical number of discrete hand hygiene events in the pediatric ward and the intensive care ward will yield completely different hand hygiene rates due to the large difference in typical hand hygiene opportunity value.

Utilization of the previously stated equation for determining hand hygiene compliance rate, which necessarily includes the number of hand hygiene opportunities, will yield a normalized hand hygiene rate which allows the comparison of hand hygiene compliance rates against a target hand hygiene compliance rate, or comparison of hand hygiene compliance rates between co-workers regardless of disparity in the number of hand hygiene opportunities characteristic of each co-worker's work area.

While globally accepted methodology for determining the hand hygiene compliance rate of individual employees or co-workers exists, historically, it has been difficult to implement in a broad and scalable fashion within large facilities or across even small groups of employees or co-workers for a variety of reasons. For example, the human observation method is cost prohibitive and non-scalable over large groups of co-workers, or across many facilities. Additionally, research has shown that hand hygiene performance or compliance rate results obtained via human observation are inaccurate due to impartiality of the observer, and other reasons such as the well known Hawthorne Effect. But perhaps more importantly, surveillance methods such as human observation which may identify and single-out discreet individuals and/or their activity are inherently difficult to implement due to co-worker rejection resulting from concerns about the invasion of their privacy and other related social issues. While electronic surveillance methods have simplified the monitoring of discreet individuals, these electronic surveillance methods do not address, and may even exacerbate co-worker concerns over invasion of privacy. Despite these challenges, human observation remains the standard method for determining the quantity of hand hygiene opportunities which has occurred over a specific period of time.

The invention disclosed herein is an improvement over electronic hygiene event surveillance or monitoring devices in that, although it utilizes data-based hygiene event data which may have been electronically acquired, it necessarily excludes utilization of data which could be used to identify or single out individual employees or co-workers in favor of group based hygiene behavior measurements. The disclosed invention is an improvement over existing devices because it handles data-based hygiene event such that the hygiene event data for groups or teams of co-workers are aggregated into a single set of hygiene events such that the aggregated data is said to be the hygiene event data for an entire and specific group or team. In this way, the disclosed invention preserves the privacy of discrete individuals while at the same time allowing for an assessment of hand hygiene performance.

The invention disclosed herein relies on the globally accepted human observation method for determining the quantity of hand hygiene opportunities which have been experienced by an employee of co-worker over a specific period of time. The disclosed invention relies on the human observation method to determine the number of hand hygiene opportunities of one or several individuals from within a group or team of co-workers, and then utilize the number or average number of hand hygiene opportunities as representative of the number of hand hygiene opportunities typically experienced by a group or team of co-workers from which the observed number or average number of hand hygiene opportunities was observed. In this manner, a typical number or typical average number of hand hygiene opportunities for an entire group or team of employees or co-workers may be determined.

The disclosed invention is a system which parses data-based hygiene event data which has been acquired from groups or teams of co-workers such that personal identification of individuals is excluded, aggregates the parsed hygiene event data into a single value for the entire group, and then utilizes an observed value or average value of hand hygiene opportunities for the group as a denominator value such that the hand hygiene compliance rate for an entire group or team of co-workers may be computed. Hand hygiene compliance, or hand hygiene performance for a group or team of co-workers which is computed in the manner disclosed herein is said to be normalized in that, for management and process control purposes, the computed hand hygiene compliance rates may be compared against target compliance rates, and comparison of hand hygiene compliance rates between semi or totally disparate groups or teams of co-workers within large facilities is enabled.

Additional research performed by several leading authorities in the area of hand hygiene including the University of Pennsylvania School of Medicine, and the Columbia University School of Nursing suggests that it is not only surveillance and monitoring of hygiene activity that is necessary to achieve a sustainable improvement in hand hygiene compliance rates of co-workers and personnel, but also that, among other things, frequent and unobtrusive feedback regarding measured hand hygiene performance against hand hygiene performance targets must also be provided to personnel and co-workers. This is not surprising because it follows that it is difficult to define and understand the meaning of performance, or performance improvement without temporal context or frequent feedback which explains how current performance compares with, or relates to expected performance.

The invention disclosed herein improves upon surveillance and monitoring hygiene data acquisition systems because not only does it provide a means for operating upon raw hygiene data, excluding data which could be used to identify individuals, performing subsequent calculation and determination of a normalized hand hygiene rate quotient, and enabling hand hygiene performance or rate to be ascertained, but the disclosed invention also provides a means for graphical rendering of the normalized group hand hygiene compliance rate data over time, and distribution of the rendered data over a computer network such as a corporate intranet, a private network, or the Internet. Distribution of a graphical or similar rendering of the normalized team hand hygiene performance or compliance rate data over a network provides a means for the displaying of team hand hygiene performance or compliance rate data on a plurality of network devices, such as monitors.

The pervasiveness of existing computer networks within modern facilities or the ease with which a new or private computer network may be established within any facility, such as a hospital, nursing home or food processing facility, enables the display of real-time, or near real-time rendered normalized team hand hygiene performance or compliance rate data at virtually any place within a facility as desired. The placement of network devices such as monitors in select areas within a facility which are frequently visited by co-workers or team members allows co-workers or team members to see the current group or team hand hygiene performance or compliance rate compared against target compliance rates and thereby receive frequent and unobtrusive feedback regarding the group's or team's hand hygiene performance or compliance rate behavior. The purpose of providing frequent and unobtrusive feedback by the disclosed invention responds directly to a substantial amount of research which has shown that frequent and unobtrusive feedback regarding hand hygiene performance must be provided to personnel in order to achieve a sustained improvement in hand hygiene performance and hand hygiene compliance rates.

The forgoing description of the system for monitoring dispensers equipped with Wireless communication devices for the purpose of determining hand hygiene performance has been presented for the purpose of illustration and description. It is not intended to be exhaustive or to limit the invention to the precise form disclosed. Many modifications and variations are possible in light of the above teachings. Pursuant to the above, it is to be understood that the drawings and descriptions herein are presented by way of example to facilitate comprehension of the invention and should not be construed to limit the scope thereof. Accordingly, any and all modifications, variations or equivalent arrangements which may occur to those skilled in the art, should be considered to be within the scope of the present invention.

What is claimed is:

1. A hand hygiene rate calculation and hand hygiene performance feedback system comprising a computer network with an application software administration center, and application software operative on the computer network which allows an application software user to direct the application software to interface with and query data or data-bases at sites or locations on the network where raw hygiene data is produced or stored, and with an application software user interface which enables the application software user to enter or choose a desired hand hygiene rate metric from a list of standard metrics, and to also input a hand hygiene rate denominator value such that execution of the application software will cause mathematical operations to be performed upon raw hygiene data from locations queried as selected by the applications software user, and utilizing the hand hygiene rate metric selected by the user and the hand hygiene rate denominator value input by the applications software user, the system will output processed data in the form of hand hygiene performance data or hand hygiene rate data.

2. The system of claim 1, wherein the application software is configurable via the application software administration center to address and interface with data-based raw hygiene data residing anywhere on the computer network that the application software is located, whether the network is a corporate intranet, a private network, or the Internet, and which raw hygiene data contains time stamped hand hygiene event data such as the number of times and when a particular soap or sanitizer dispenser or group of particular soap or sanitizer dispensers have been used, and is stored in a publicly available database format.

3. The system of claim 2, wherein the application software is configured to perform mathematical operations on raw hygiene data such that only the raw data required to assess the hand hygiene performance or hand hygiene compliance rate of a group or team of co-workers or personnel from which the raw data originated is operated upon, and which raw data includes time stamped soap or sanitizer dispenser usage data such as the number of times and when a particular soap or sanitizer dispenser or group of particular soap or sanitizer dispensers have been used, and such that any personnel identification information and any other information which links individual personnel identification to the raw data is necessarily excluded from mathematical operation by the application software.

4. The system of claim 1, wherein the application software is configurable via the application software administration center to address and interface with data-based raw hygiene data residing anywhere on the computer network that the application software is located, whether the network is a corporate intranet, a private network, or the Internet, and where the data-base contains raw hygiene data that has been acquired by any electronic or automated personnel hygiene surveillance or monitoring system, and which raw hygiene data contains time stamped hand hygiene event data such as the number of times and when a particular soap or sanitizer dispenser or group of particular soap or sanitizer dispensers have been used, and is stored in a publicly available database format.

5. The system of claim 4, wherein the application software is configured to perform mathematical operations on raw hygiene data such that only the raw data required to assess the hand hygiene performance or hand hygiene compliance rate of a group or team of co-workers or personnel from which the raw data originated is operated upon, and which raw data includes time stamped soap or sanitizer dispenser usage data such as the number of times and when a particular soap or sanitizer dispenser or group of particular soap or sanitizer dispensers have been used, and such that any personnel identification information and any other information which links individual personnel identification to the raw data is necessarily excluded from mathematical operation by the application software.

6. The system of claim 1, wherein the application software user interface includes:

a field (14) where the user inputs or selects from a list of standard hand hygiene performance or hand hygiene rate metrics the hand hygiene performance or hand hygiene rate metrics or units which are to be assigned to the processed and output hand hygiene performance or hand hygiene rate data, and which includes at least one of the following: hand washes or hand wash events per employee hour, hand washes or hand wash events per meal served, hand washes or hand wash events per average opportunity, hand washes or hand wash events per hospital bed-day, hand washes or hand wash events per patient-hour, and hand washes or hand wash events per hospital patient-day;

a field (15) where a time period is defined by the user such that only the raw hygiene data belonging to the defined period will be operated upon, and therefore the application software output will be hand hygiene performance data or hand hygiene rate data belonging only to the defined time period;

a field (15) where a numerical denominator value having units or metrics which match those as chosen by the user (14) are input into the system by the user;

a field (16) where the user inputs or selects from a list the desired rendering or format of the post execution processed data output;

a field (15) from within which the application software is executed such that the application software uses the parameters which have been selected and input into the application software user interface, and which causes the post execution processed data output to be saved on a network computer (6).

7. The system of claim 6, wherein the application software accepts the definition of a time period with an end point in the future such that the application software will automatically continue to operate upon raw hygiene data until such future end point is reached, and so that the application software output will be hand hygiene performance or hand hygiene rate data which is automatically and periodically updated as new raw hygiene data becomes available.

8. The system of claim 7, wherein the application software output is hand hygiene performance or hand hygiene rate data in real-time when the raw hygiene data is available in real-time.

9. The system of claim 6, wherein when the application software has been configured by the user via the application software user interface to use one of the standard hand hygiene metrics appearing in a list within the application software user interface (14), and when the application software has been sufficiently provided with a time period and numerical denominator value (15), the execution of the application software will cause mathematical operations which are characteristic to the application software to occur and operate upon queried raw hygiene data such that the output of the system is processed hand hygiene performance, or hand hygiene rate data which is saved in a data-base on a network computer (6).

10. The system of claim 9, wherein the execution of the application software performs the mathematical operations characteristic to the application software upon raw hygiene data such that only the raw data required to assess the hand hygiene performance or hand hygiene compliance rate of a group or team of co-workers or personnel from which the raw data originated is operated upon, and which includes time stamped soap or sanitizer dispenser usage data such as the number of times and when a particular soap or sanitizer dispenser or group of particular soap or sanitizer dispensers has been used, and such that any personnel identification information and any other information which links individual personnel identification to the raw data is necessarily excluded from mathematical operation by the application software such that the post execution output of the application software is characteristic of the group or team of co-workers from which the raw data has originated.

11. The system of claim 10, wherein the mathematical operations performed by the application software upon the raw hygiene data are mathematical or statistical analysis operations.

12. The system of claim 11, wherein when the application software performs the mathematical operation of division, whereby the raw hygiene data that was queried by the application software and subsequently parsed to exclude personnel identification information is combined into a single value and then divided by the numerical denominator value entered by the user (15), such that the execution of the application software yields an output which is a hand hygiene performance or hand hygiene rate quotient of the combined value in the form of a percentage or percentage decimal equivalent.

13. The system of claim 6, wherein that the application software user interface includes a field (16) for choosing the output format or rendering of the processed hand hygiene performance, or hand hygiene rate data from a list which includes a graphical and tabular rendering of output data.

14. The system of claim 13, wherein when a tabular output is selected, the system output of hand hygiene performance or hand hygiene rate data is displayed in a table and is visible via the application software user interface.

15. The system of claim 13, wherein when a graphical output is selected, the system output of hand hygiene performance or hand hygiene rate data are plotted over a discreet period of time (15), where the ordinate axis has units or metrics as entered or selected by the user via the application software user interface (14) and the abscissa has units of time, and the resulting plot is displayed graphically and visibly via the application software user interface.

16. The system of claim 15, wherein the graphical output display also includes one or two horizontal lines which are independent of the plotted output data values and have fixed, user defined ordinate values such that when a single horizontal line is present, the single horizontal line represents a user defined minimum hand hygiene performance or hand hygiene rate target value, or represents a user defined target hand hygiene performance or hand hygiene rate value, and such that when two said horizontal lines are present one of the horizontal lines represents a user defined minimum hand hygiene performance or hand hygiene rate value, and the second horizontal line represents a user defined target hand hygiene performance or hand hygiene rate value.

17. The system of claim 16, wherein the horizontal lines represent user defined hand hygiene process control limits such as are commonly used in statistical process control methods and provide a means for observing the hand hygiene performance or hand hygiene rate data of groups or teams of co-workers as hand hygiene process output data whereby the plotted hand hygiene performance data or hand hygiene rate data of the group or team of co-workers is plotted over time, and is therefore plotted within the defined, fixed process control limits, or outside of the defined, fixed process control limits.

18. The system of claim 6, wherein the system output, such as a graphical rendering of the group or team hand hygiene performance or hand hygiene rate, is distributed to any user or computer or central processing unit on the computer network (4) whether the network is a corporate intranet, a private network, or the Internet, and which has been granted appropriate access and permissions via the application software administration center.

19. The system of claim 18, wherein any number of computers or display devices with central processing units are distributed and situated such that, during their normal workday functions, the computer monitors or display devices with central processing units are in the frequent and periodic view of the group or team of co-workers from which the raw hygiene data upon which the application software operates has originated, and such that group or team hand hygiene performance data or data rendering is visible by the group or team of co-workers as hand hygiene performance or hand hygiene rate feedback to the group or team of co-workers.

20. The system of claim 6, wherein any of the recited fields may be populated or selected or executed automatically and without human intervention by a second software application operating on the same computer network as the system of claim 6 whether the computer network is a corporate intranet, a private network, or the Internet, and which characteristically and automatically collects such information as a part of the normal function of said second application software.

\* \* \* \* \*

UNITED STATES PATENT AND TRADEMARK OFFICE
CERTIFICATE OF CORRECTION

PATENT NO. : 7,855,651 B2
APPLICATION NO. : 12/634408
DATED : December 21, 2010
INVENTOR(S) : LeBlond et al.

It is certified that error appears in the above-identified patent and that said Letters Patent is hereby corrected as shown below:

In the Drawings

Please delete Drawing Sheet 7 of 13 and substitute the attached Drawing Sheet 7 of 13.

Please delete Drawing Sheet 11 of 13 and substitute the attached Drawings Sheet 11 of 13.

Signed and Sealed this
Third Day of May, 2011

David J. Kappos
*Director of the United States Patent and Trademark Office*

FIGURE 11